United States Patent
Turner et al.

(10) Patent No.: US 11,738,127 B2
(45) Date of Patent: Aug. 29, 2023

(54) EXCHANGER FOR MEDICAL USE

(71) Applicant: Spectrum Medical Group Limited, Gloucester (GB)

(72) Inventors: Stephen Turner, Cheltenham (GB); Daniele Galavotti, Mirandola (IT)

(73) Assignee: SPECTRUM MEDICAL GROUP LIMITED, Gloucester (GB)

( * ) Notice: Subject to any disclaimer, the term of this patent is extended or adjusted under 35 U.S.C. 154(b) by 573 days.

(21) Appl. No.: 16/753,771

(22) PCT Filed: Oct. 5, 2018

(86) PCT No.: PCT/EP2018/025258
§ 371 (c)(1),
(2) Date: Apr. 4, 2020

(87) PCT Pub. No.: WO2019/068370
PCT Pub. Date: Apr. 11, 2019

(65) Prior Publication Data
US 2020/0282118 A1 Sep. 10, 2020

(30) Foreign Application Priority Data
Oct. 5, 2017 (IT) .................. 102017000111990

(51) Int. Cl.
*A61M 1/36* (2006.01)
*A61M 1/16* (2006.01)
(Continued)

(52) U.S. Cl.
CPC ............ *A61M 1/1698* (2013.01); *A61M 1/36* (2013.01); *A61M 60/113* (2021.01); *A61M 60/38* (2021.01); *A61M 2205/366* (2013.01)

(58) Field of Classification Search
None
See application file for complete search history.

(56) References Cited

U.S. PATENT DOCUMENTS

2002/0044889 A1* 4/2002 Aboul-Hosn ....... A61M 1/3667
604/6.14
2006/0177343 A1 8/2006 Brian, III et al.
(Continued)

FOREIGN PATENT DOCUMENTS

| WO | WO02/1004725 | 12/2002 |
| WO | WO2015/100288 | 7/2015 |
| WO | WO2018/002622 | 1/2018 |

OTHER PUBLICATIONS

International Search Report and Written Opinion of PCT/EP2018/025258 dated Jul. 3, 2019, 22 pages.

*Primary Examiner* — Ankit D Tejani
(74) *Attorney, Agent, or Firm* — Rankin, Hill & Clark LLP (57) ABSTRACT

An exchanger for medical use comprises: a box-like body having a base, an upper end, a peripheral wall that delimits a heat exchange chamber; the body having: a first aperture from which a fluid to be thermo-regulated enters and a first exit of the thermo-regulated fluid; a second delivery aperture of a thermo-regulator fluid and a second exit of the thermo-regulated fluid; a heat exchange element that exchanges heat by lapping, housed in the exchange chamber and held between two holding elements, dividing the exchange chamber into a zone where the thermo-regulator fluid flows and a zone where the fluid to be thermo-regulated flows, which are fluid-dynamically separated from each other; a collection compartment to collect the air separated from the fluid to be thermo-regulated, obtained in the opposite end, connected to the thermo-regulation chamber and equipped with an aperture toward the outside; the box-like body has a second housing chamber for a pumping group, connected with the heat exchange chamber.

16 Claims, 6 Drawing Sheets

(51) Int. Cl.
*A61M 60/113* (2021.01)
*A61M 60/38* (2021.01)

(56) References Cited

U.S. PATENT DOCUMENTS

2010/0272605 A1  10/2010  McIntosh et al.
2017/0361011 A1* 12/2017  Muennich ........... A61M 1/3666

* cited by examiner

FIG. 8

EXCHANGER FOR MEDICAL USE

FIELD OF THE INVENTION

The invention concerns an exchanger for medical use, generally usable in an extracorporeal circulation line to thermally adjust an organic fluid, specifically, but not exclusively, blood.

BACKGROUND OF THE INVENTION

Heat exchangers are known which are used in the medical field to treat a patient's blood when an extracorporeal circuit is applied to the patient.

Typically, an extracorporeal circuit comprises a pipe to drain the blood from the patient that has one end which is connected to a point where the blood is taken from the patient's body and which extends to define a return pipe connected to a point of the patient's body through which the treated blood is reintroduced into the circulatory apparatus.

Along the pipe, devices are disposed that are to be used to treat the blood and that typically comprise a filter to filter the blood, a circulation pump, a heat exchanger that the blood has to pass through so that the treated blood returns to the patient at a temperature compatible with body temperature to prevent thermal shock, and an oxygenator.

Along the pipe of the extracorporeal circuit, other devices can be mounted to check the parameters of the blood during its passage in the extracorporeal circuit, or to administer drugs to the patient and perform rehabilitative therapies, or again to eliminate dangerous air bubbles possibly generated during treatment of the blood.

Typically, all the devices that are provided along the pipe of an extracorporeal circuit are separated from each other and are disposed in succession, so that each progressively produces the desired therapeutic effect.

This state of the art has a series of disadvantages.

A first disadvantage is that an extracorporeal circuit which requires numerous devices to treat a patient's blood is substantially bulky, which hinders the maneuvers of the health workers during the use of the extracorporeal circuit to check the blood parameters or to administer drugs and perform therapies.

On the contrary, it would be desirable for an extracorporeal circuit to have a high overall compactness, in order not to have pipes or devices disposed in the space surrounding the place where the patient is lying and where the medical staff are working.

Another disadvantage is that the blood to be treated must make numerous passages through devices located in series and this causes an increase in the risk of generating air bubbles during the treatment and circulation in the extracorporeal circuit.

The generation of air bubbles is an extremely dangerous condition for the patient, due to the numerous joints, typically rescate connection and/or Luer fittings, needed to connect the inputs and outputs of the segments of pipe that connect the various devices one after the other and that form the extracorporeal circuit.

It is well known, in fact, that every joint can be a critical point for sealing and safeguarding the aseptic nature of the whole extracorporeal circuit and, therefore, the presence of a high number of joints determines a risk of damage to the joints themselves which is proportionally high and a consequent equally high risk for the safety of the patients.

Another disadvantage is that in an extracorporeal circuit, at least one collection chamber must be provided for the air which is eliminated from the pipe by means of a structural trapping and specific segregation geometry and/or a filter; typically, for this collection, it is necessary to prepare a collector along the circuit which is equipped with a port to discharge the collected air to the outside.

The collector is also normally made in the form of a separate container into which converge the pipes through which the air separated from the blood passes.

Therefore, in this case too there are further problems of bulk and general compactness of the extracorporeal circuit.

Another disadvantage is that for the execution of specific therapies, typically those that last for a few days and not just for a few hours and in which it is necessary to monitor the dynamic behavior of one of the devices of the extracorporeal circuit, normally the oxygenator, the oxygenator and the heat exchanger must be separated from each other, to prevent dynamic interference between them and to replace, if necessary, only one of the two, for example only the oxygenator which is the most expensive component.

Another disadvantage is that known heat exchangers are typically made of plastic material, with a low thermal exchange efficiency, susceptible to degradation of the material they are made of when they are put in contact and fed with a thermo-regulating liquid to which disinfectant solutions have been added, normally based on hydrogen peroxide, and/or bacteriostatic solutions that can spread in an uncontrolled and potentially dangerous manner through the plastic walls of the capillaries of the heat exchanger until they reach the blood of the patient treated in transit in the device.

Another disadvantage is that heat exchangers are normally fed with thermostated baths in which non-sterile water circulates, in a circuit that is open to the environment, and in the event of significant degradation of the construction materials or mechanical failure of some parts of the heat exchanger, the non-sterile thermostating water can spread uncontrollably and very dangerously in the circuit where the blood flows, causing massive hemolysis and putting the patient's safety in serious danger.

SUMMARY OF THE INVENTION

The purpose of the invention is to improve the state of the art.

Another purpose of the invention is to provide an exchanger for medical use which has a compact structure and is extremely manageable.

Another purpose of the invention is to provide an exchanger for medical use which incorporates in itself some of the main functions of an extracorporeal circuit which are normally performed with separate individual devices.

Another purpose of the invention is to provide a heat exchanger for medical use which gives the maximum guarantee in relation to safety for patients during use.

According to one aspect of the invention, an exchanger for medical use is provided, according to the characteristics of claim 1.

Other structural aspects of the invention are contained in the dependent claims.

The invention allows to obtain the following advantages:
to considerably simplify the structure of an extracorporeal circuit;
to combine several functions into a single device intended to be mounted on an extracorporeal circuit;

to considerably reduce the connection points and, consequently, the risks of damage to the extracorporeal circuit and accidental entry of air into the latter.

BRIEF DESCRIPTION OF THE DRAWINGS

Other characteristics and advantages of the invention will become more apparent from the detailed description of preferred but non-exclusive embodiments of an exchanger for medical use, shown by way of non-restrictive example in the attached drawings wherein.

DETAILED DESCRIPTION OF A PREFERRED EMBODIMENT

In the following description, the blood is indicated as an organic fluid to be thermo-regulated while the nature of the thermo-regulating fluid is left to the choice of the person of skill in the art.

Figure 1:
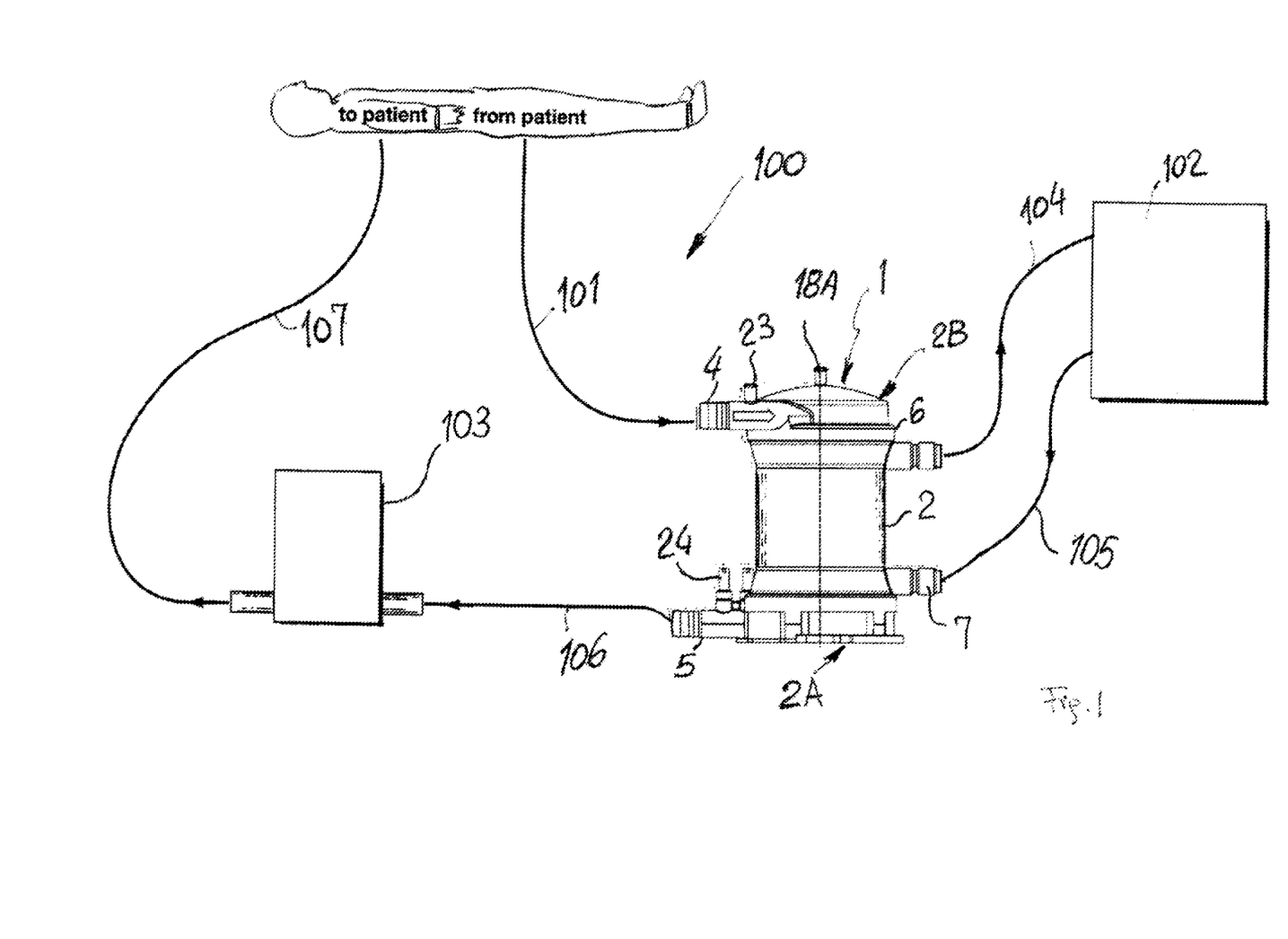
FIG. 1 is a schematic view of a first possible version of an extracorporeal circuit in which an exchanger for medical use according to the invention is inserted.

With reference to FIG. 1, a first version of an extracorporeal circuit 100 is shown.

The extracorporeal circuit 100, hereafter circuit 100 for short, comprises a line 101 to drain the blood from a patient which flows into a exchanger 1 for medical use according to the invention.

The circuit 100 also comprises a thermo-regulation device 102 and an oxygenator 103 located downstream of the exchanger 1.

Between the thermo-regulation device 102 and the exchanger 1, connection lines 105 are provided from the thermo-regulation device 102 to the exchanger 1 and 104 from the latter returning to the thermo-regulation device 102.

Starting from the exchanger 1, a line 106 connects it at entrance to the oxygenator 103 and from the latter a line 107 departs, returning to the patient and re-infusing the treated blood.

Figure 2:
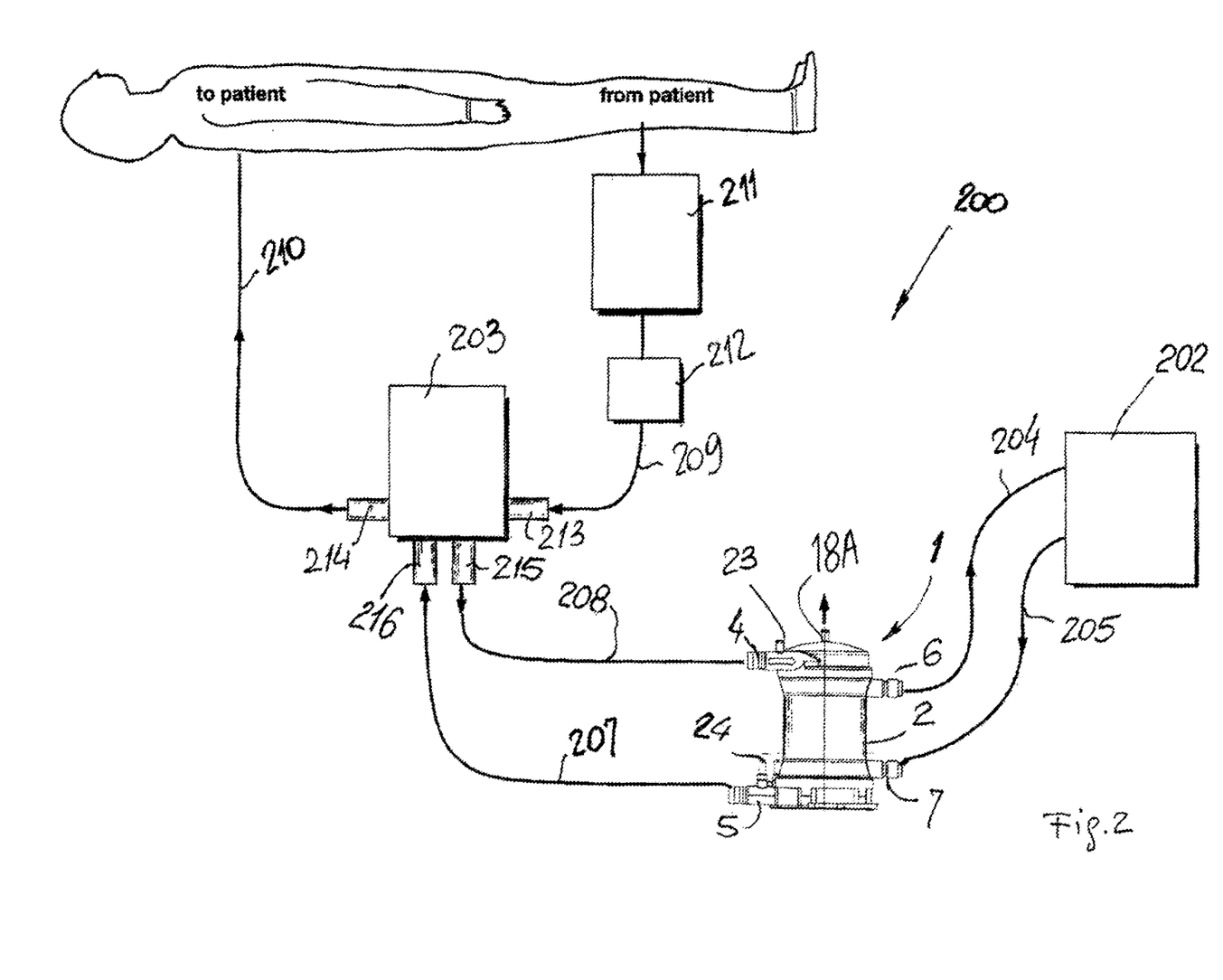
FIG. 2 is a schematic view of a second possible version of an extracorporeal circuit in which an exchanger for medical use according to the invention is inserted.

With reference to FIG. 2, there is a second version of an extracorporeal circuit 200, hereafter referred to as circuit 200 for short.

In this case the circuit 200 also comprises the exchanger 1, a thermo-regulation device 202 and an oxygenator 203, located downstream of the exchanger 1.

The fluid connections between the regulation device 202 and the exchanger 1 are made with a delivery line 205 and a return line 204.

The connection between the exchanger 1 and the oxygenator 203 is also provided with a delivery line 207 and a return line 208 which are connected to respective ports 216 and 215.

Two more lines are connected to the oxygenator 203, namely a drain line 209 to drain blood from the patient and a return and re-infusion line 210 to return the treated blood to the patient, which are connected to respective ports 213 and 214.

On the drain line 209 a tank 211 and a pumping group 212 are also mounted.

In the first version of the circuit 100, the blood flows inside the lines 101, 106, 107 while the thermo-regulating fluid flows inside the lines 104 and 105.

In the second version of the circuit 200, the thermo-regulating fluid again flows inside the lines 204 and 205 while an aseptic fluid, for example sterile water, flows, if appropriate, inside the lines 207 and 208, and the patient's blood flows in the lines 209 and 210.

In both versions of the extracorporeal circuit 100 or 200, the fluids flowing in the exchanger 1 always flow in opposite directions with respect to each other.

Figure 3:
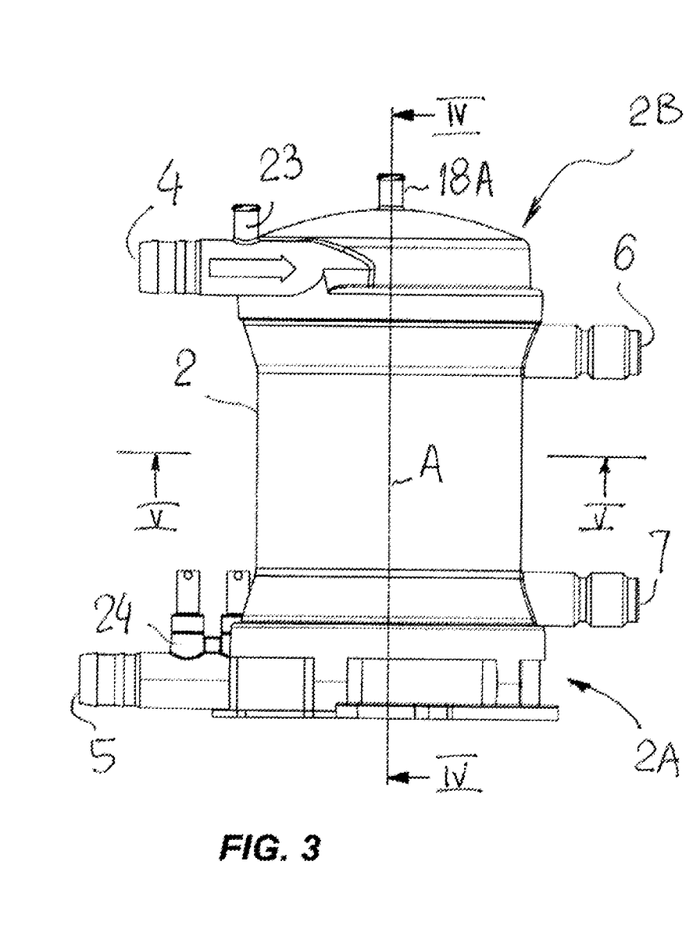
FIG. 3 is an overall lateral view of an exchanger for medical use according to the invention.
Figure 4:
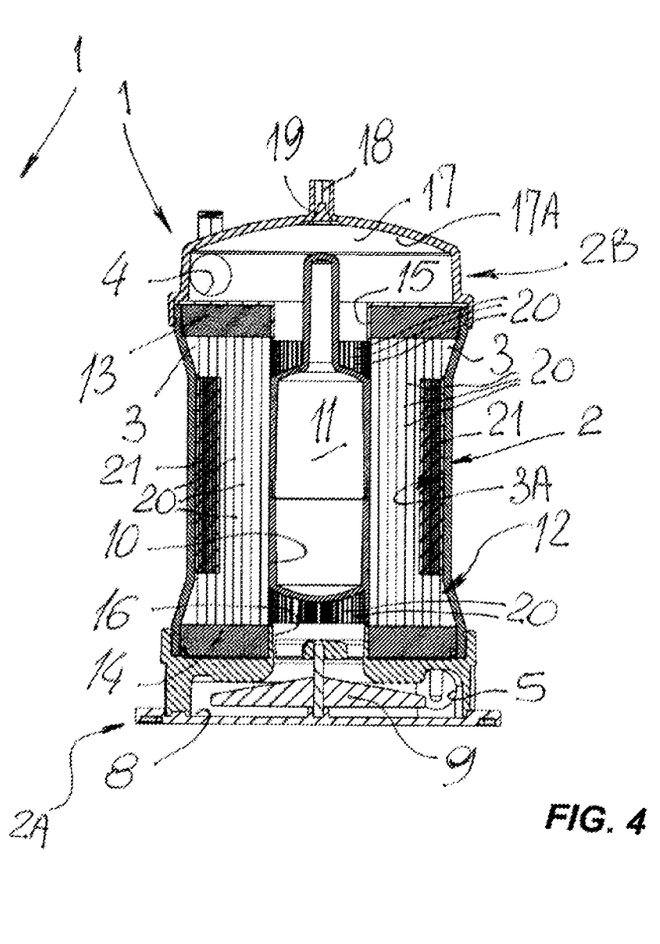
FIG. 4 is a vertical section view of the exchanger in FIG. 3, taken according to a plane IV-IV.

With reference to FIGS. 3 and 4, it can be seen that the exchanger 1 for medical use according to the invention comprises a box-like body 2, preferably cylindrical in shape, inside which a heat exchange chamber 3 is defined, indicated for short below as first chamber 3, delimited on the perimeter by an internal wall 3A.

The container body 2 has a central longitudinal axis "A" and comprises a series of apertures, namely a first aperture 4 which, in the first version of the circuit 100, serves as an entrance for a fluid to be thermo-regulated, for example blood drained from the patient, and a first exit 5 for the thermo-regulated blood.

The body 2 also comprises a second aperture 6 for the delivery of a thermo-regulating fluid toward the thermo-regulation device 102 and a second aperture 7 for the entrance of the thermo-regulating fluid after it has been thermo-regulated.

As can be seen in the drawings, all the apertures 4-7 indicated above are provided with respective extensions toward the outside, disposed to allow the connection and the end attachment of the lines 101, 104, 105, 106, 107 which are all made in the form of pipes in which the thermo-regulating fluid and the blood to be treated flow separately from each other.

A second chamber 8 is also made in the body 2, positioned in a part considered as the base 2A of the body 2, in which a pumping group 9 is housed which, as will be described in detail below, has the function of draining the flow of blood from the patient and, in the configuration of the circuit 100, of pumping it inside the oxygenator or in the configuration of the circuit 200, of recirculating sterile water inside the exchanger usually integrated in the oxygenator 203.

The second chamber 8 is disposed coaxially with the heat exchange chamber 3 and communicates with it by means of a central channel 10, cylindrical and coaxial with the axis "A".

In the central channel 10 a flow diverter 11 is housed, disposed to divert the flows of fluid entering, blood or sterile water, toward a heat exchange element 12, three-dimensional, better described hereafter, which is disposed inside the first chamber 3 and which is held in the latter by means of two coaxial sealing rings 13 and 14 which shape respective central apertures 15 and 16, coaxial with each other; the sealing rings 13 and 14 are kept in contact and sealed with the internal wall 2A.

In the part of the body 2 opposite the base 2A, that is, in the part 2B of the body 2 considered as the upper part, a compartment 17 for collecting air is made, which may possibly be present in the blood, in the water or in a sterile saline solution to be thermo-regulated, and in the form of bubbles.

The compartment 17 has a dome-shaped top 17A and in the top of it an aperture 18 is provided, which puts it in communication with the outside and which, like the other apertures described above, is provided with an extension 18A disposed for the connection of a pipe to remove the air (not visible in the drawings).

Figure 7:
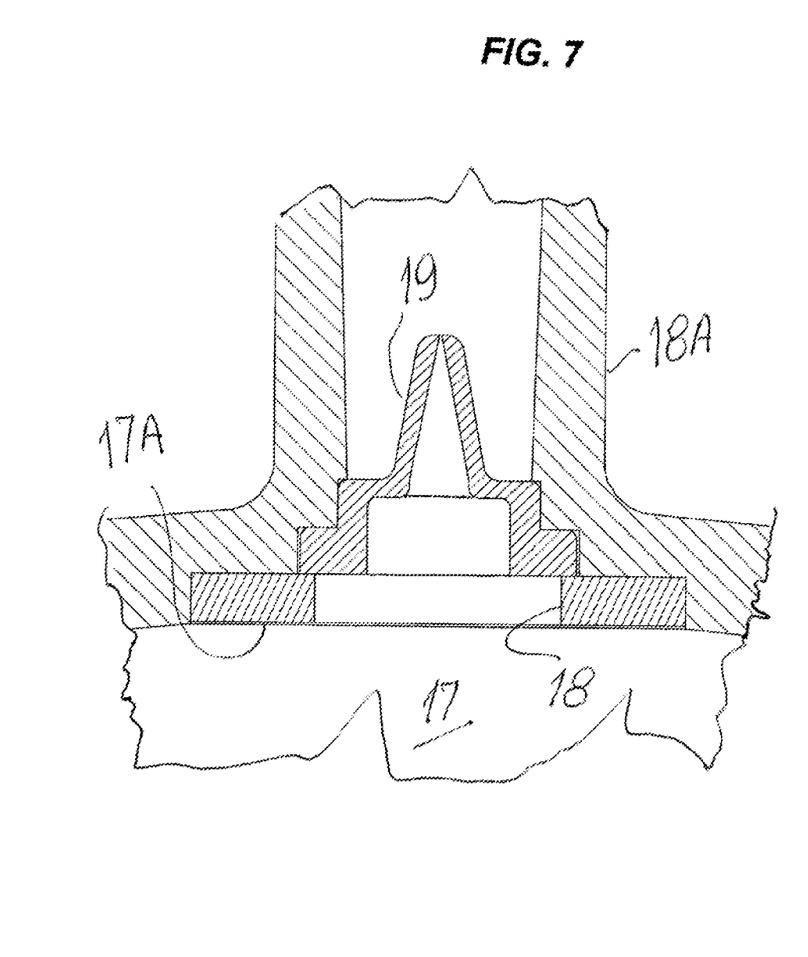
FIG. 7 is a view of a detail in greatly enlarged scale of a part of the exchanger in FIG. 4.

As shown in FIG. 7, the aperture 18 is controlled by a valve diaphragm, in this specific case a lip valve 19 made of plastic material which is suitable to open or close the passage alternately, allowing only the air or liquid mixed with air to be aspirated, toward the outside and not vice versa.

The heat exchange element 12 consists of a lamellar body, preferably made of stainless steel with high thermal conductivity, which generally has a substantially cylindrical shape, but which could also have other solid geometric shapes.

Figures 5, 6:
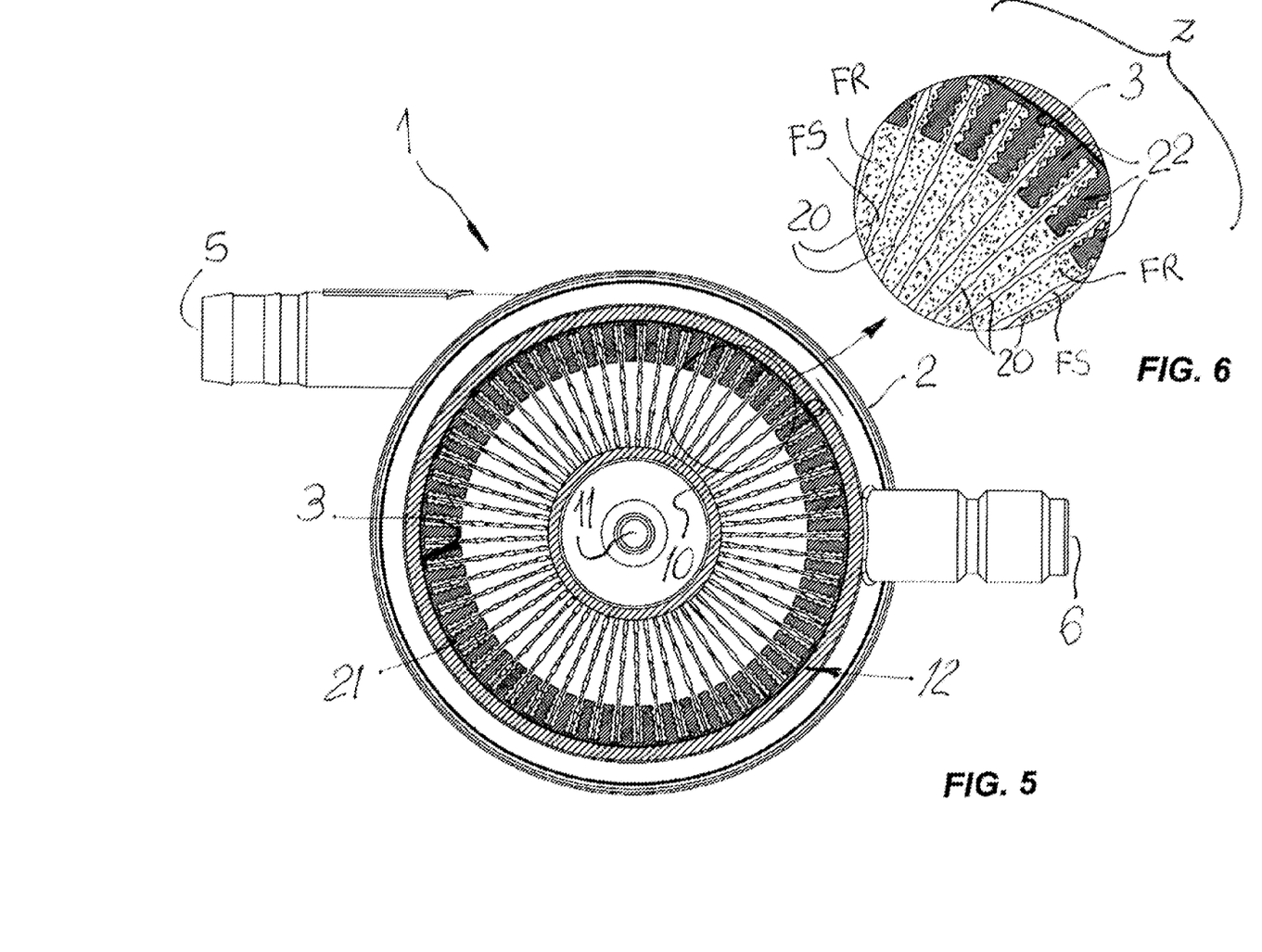
FIG. 5 is a cross-section view of the exchanger in FIG. 1, taken according to a plane V-V.
FIG. 6 is an enlarged scale view of a portion of FIG. 5.

In detail, the heat exchange element 12 is formed by a plurality of ribs 20 bent accordion-like and oriented radially with respect to the central pipe 10.

All the ribs 20 are formed in succession and without a break in continuity of the lamellar body.

Figure 8:
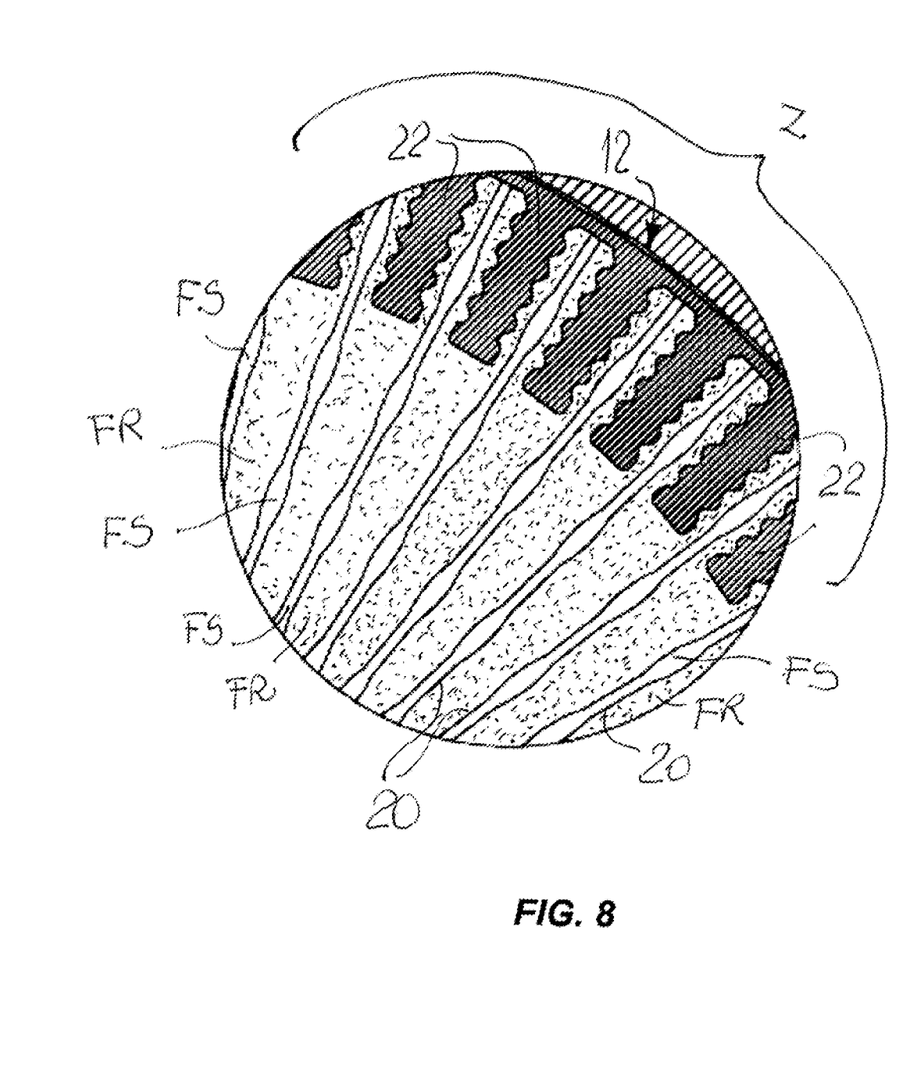
FIG. 8 is a view in greatly enlarged scale of a portion of FIG. 6.

Between adjacent ribs 20 zones of alternate passage of blood, or water or a sterile saline solution, and of a thermo-regulating fluid are defined: to make this characteristic clearer, in FIGS. 6 and 8 an angular sector "Z" of the heat exchange element has been selected in detail, in which the zones "FR" where the thermo-regulating fluid passes are indicated with a plurality of dots, while the clear zones "FS" are those in which the blood to be thermo-regulated or the sterile water flows.

Both flow in a direction perpendicular to the observation plane of the drawings, between the upper part 2B and the lower part 2A, but in opposite senses or, according to a technical definition, counter-current.

As can be seen, each rib 20 is therefore a separating diaphragm which has a thickness of a few tenths of a millimeter and which separates the zones "FR" and "FS" in a sealed manner.

The opposite surfaces of each rib 20 are respectively lapped by the blood or the water or a sterile saline solution, and by the thermo-regulating fluid which performs its thermo-regulating action by contact with the surfaces of the ribs 20 from which it is then transmitted to the blood or to the sterile water.

In order to keep the ribs 20 equally distanced, spacer means are provided which are wound outside the heat exchange element and which engage the ribs 20.

The spacer means are made in the form of at least one cylindrical element 21 which is disposed between the internal wall 3A and the heat exchange element and which, on an internal face 21A, is provided with a series of second ribs 22 which extend in relief from this in a centripetal direction, that is, toward the central channel 10, positioning themselves for a limited distance between the outwardly facing ends of adjacent ribs 20.

Advantageously, in order to improve the heat exchange efficiency and increase the fluidic turbulence between the second ribs 22 and the surfaces of the ribs 20, a regular or random succession of reliefs and channels can be provided on the surfaces of both, but are not visible in the drawings.

It should be noted that the apertures 4 and 5 are also provided with access ports 23 and 24, respectively, to allow the first chamber 17 to be filled, so-called "priming" and allow the insertion of devices to control the parameters of the thermo-regulating fluid, for example to detect the temperature at outlet.

The functioning of the exchanger for medical use is described below, for both versions of the two extracorporeal circuits 100 and 200.

In the case of the circuit 100, the exchanger 1 is mounted upstream of the oxygenator 103.

Before use, in the body 2 a filling (or so-called priming) of blood to be thermo-regulated is performed, introducing it through the port 23 provided for this purpose.

To promote drainage from the patient, the pumping group 9 is made to function, creating a depression inside the first chamber 3.

This depression promotes the drainage of blood from the patient, which enters the first chamber 3 through the first aperture 4, passes through the central aperture 15 of the ring 13 and is diverted by the flow diverter 11 in a radial direction, occupying and flowing in the zones "FS" defined between the ribs 20.

At the same time, the thermo-regulating fluid is sent to the thermo-regulation device 102 through the second delivery aperture 6 and, after it has been thermo-regulated, it is introduced inside the exchanger 1 through the second aperture 7, flowing in the zones "FR", but in the opposite direction to the flow of blood flowing in the zones "FS".

In this way, the temperature of the thermo-regulating fluid is transmitted by contact to the surfaces of the ribs 20 and from this, again by contact, to the blood to be thermo-regulated, before being sent to the oxygenator 103 and subsequently re-infused into the patient.

During treatment, the air possibly present in the form of micro-bubbles in the blood to be treated is collected inside the compartment 17 and from this compartment it is then expelled toward the outside, causing the valve 19 to open, for example, by applying a suction force to the aperture 18 by means of a conventional suction device connected to the latter.

If it is necessary to detect some parameters concerning the treated blood, it is possible to insert a probe, or an equivalent detection device, in the access port 24 in a sealed manner.

In the case of the second version of the circuit 200, the functioning of the exchanger 1 is the same as that described above for the first version of the circuit 100, with the only difference that the circulation of the blood flow is replaced by the circulation of the flow of water or a sterile saline solution.

The flow of water or a sterile saline solution arrives from the oxygenator 203 through the line 208, enters the exchanger 1 from the first aperture 4, continues the path along the central channel 10, expands inside the zones "FS" and exits from the first exit aperture 5 to return, after being thermo-regulated, to the oxygenator 203 through line 207.

Inside the oxygenator 203 a second heat exchange takes place between the flow of water or a sterile and thermo-regulated saline solution and the drained blood which passes through it, before being re-infused into the patient.

It should be noted that in this second version of the circuit 200, the water or a sterile saline solution follows a hermetically closed path between the exchanger 1 and the oxygenator 203, which makes the heat exchange totally contamination-free and safe even in the event of structural failures of the heat exchanger integrated into the oxygenator, because even if the sterile saline solution is diffused in the circulating blood the only inconvenience for the patient would be a slight dilution of the blood, without any danger whatsoever of contamination or, even worse, hemolysis of the red cells.

In practice it has been found that the invention achieves the intended purposes.

The invention as conceived is susceptible to modifications and variations, all of which come within the concept of the invention.

Furthermore, all the details can be replaced with other technically equivalent elements.

In practical implementation, any materials, shapes and sizes can be used, according to requirements, without for this reason abandoning the field of protection of the following claims.

The invention claimed is:

1. An exchanger for medical use comprising:
    a box-like body having a base, an opposite upper end, a peripheral wall and inside which a thermal exchange chamber is defined, delimited by an internal surface of the peripheral wall, said body having:
    at least one first entrance aperture of a fluid to be thermo-regulated and a first exit of thermo-regulated fluid;
    a second delivery aperture of a thermo-regulator fluid and a second exit of said thermo-regulated fluid;
    a heat exchange element by lapping that is housed in said exchange chamber and retained between two holding elements and which divides said exchange chamber into a zone where the thermo-regulator fluid flows and a zone where the fluid to be thermo-regulated flows and which are fluid-dynamically separated from each other;
    a collecting compartment of air separated from said fluid to be thermo-regulated, obtained in said opposite end and connected to said exchange chamber and equipped with an aperture communicating with the outside,
    wherein said box-like body defines a second housing chamber fora pumping group and in fluid-dynamical connection with said heat exchange chamber,
    wherein said heat exchange element comprises a lamellar body that shapes a plurality of contiguous ribs and which has overall a cylindrical/three-dimensional shape and defines said flow passage zones of said thermo-regulator fluid and said passage zones of said fluid to be thermo-regulated, fluid-dynamically separated from each other,
    wherein said lamellar body is folded in accordion fashion and comprises spacer means interposed between the ribs.

2. Exchanger as in claim 1, wherein said second chamber is obtained in said base.

3. Exchanger as in claim 2, wherein said spacer means comprise at least one cylindrical element that is wound around said heat exchange element externally and that is equipped on an inner face with a series of second ribs in relief, facing centripetally toward said ribs, each second rib being at partly interposed between two adjacent ribs.

4. Exchanger as in claim 1, wherein said heat exchange element is made of a stainless metal material.

5. Exchanger as in claim 1, wherein said holding elements comprise two sealing rings which are attached to the ends of said lamellar body and which have respective external surfaces in sealing contact with said internal wall of said heat exchange chamber.

6. Exchanger as in claim 5, wherein said sealing rings shape respective central coaxial apertures for the passage of said fluid to be thermo-regulated.

7. Exchanger as in claim 6, wherein between said central apertures a central cylindrical passage is defined for the passage of said fluid to be thermo-regulated and in which a flow diverting member of said fluid to be thermo-regulated is housed.

8. Exchanger as in claim 7, wherein said central cylindrical channel is connected to said second housing chamber.

9. Exchanger as in claim 1, wherein said spacer means comprise at least one cylindrical element that is wound around said heat exchange element externally and that is equipped on an inner face with a series of second ribs in relief, facing centripetally toward said ribs, each second rib being at least partly interposed between two adjacent ribs.

10. Exchanger as in claim 9, wherein said second ribs have surfaces provided with a regular or random succession of reliefs and ducts to corresponding surfaces of said ribs.

11. Exchanger as in claim 9 wherein said second ribs each extend radially inwardly only along a portion of said adjacent ribs.

12. Exchanger as in claim 11, wherein said spacer ribs extend from an inner face of at least one cylindrical element that is wound around said heat exchange element externally, said spacer ribs facing centripetally toward said ribs, each spacer rib being at least partly interposed between two adjacent ribs.

13. Exchanger as in claim 12 wherein said second ribs each extend radially inwardly only along a portion of said adjacent ribs.

14. Exchanger as in claim 12 wherein each second rib is circumferentially spaced apart from said two adjacent ribs.

15. Exchanger as in claim 9 wherein each second rib is circumferentially spaced apart from said two adjacent ribs.

16. An exchanger for medical use comprising:
    a body having a base, an opposite upper end, a peripheral wall and inside which a thermal exchange chamber is defined, delimited by an internal surface of the peripheral wall, said body having:
    at least one first entrance aperture of a fluid to be thermo-regulated and a first exit of thermo-regulated fluid;
    a second delivery aperture of a thermo-regulator fluid and a second exit of said thermo-regulated fluid;
    a heat exchange element by lapping that is housed in said exchange chamber and retained between two holding elements and which divides said exchange chamber into a zone where the thermo-regulator fluid flows and a zone where the fluid to be thermo-regulated flows and which are fluid-dynamically separated from each other;
    a collecting compartment of air separated from said fluid to be thermo-regulated, obtained in said opposite end and connected to said exchange chamber and equipped with an aperture communicating with the outside,
    wherein said box-like body defines a second housing chamber fora pumping group and in fluid-dynamical connection with said heat exchange chamber,
    wherein said heat exchange element comprises a lamellar body that defines a plurality of circumferentially spaced apart ribs defining circumferentially alternating and spaced apart flow passage zones including flow passage zones of said thermo-regulator fluid and passages zones of said fluid to be thermo-regulated,
    wherein said lamellar body is folded in accordion fashion and comprises spacer ribs interposed between the circumferentially spaced apart ribs.

* * * * *